United States Patent [19]
Oda

[11] Patent Number: 5,523,468
[45] Date of Patent: Jun. 4, 1996

[54] PROCESS FOR PRODUCING AROMATIC PEROXYCARBOXYLIC ACIDS

[75] Inventor: Yoshiaki Oda, Osaka, Japan

[73] Assignee: Sumitomo Chemical Company, Limited, Osaka, Japan

[21] Appl. No.: 341,901

[22] Filed: Nov. 15, 1994

[30]     Foreign Application Priority Data

Nov. 16, 1993  [JP]  Japan ................................. 5-286607
Oct. 7, 1994   [JP]  Japan ................................. 6-244284

[51] Int. Cl.$^6$ ............................................. C07C 409/30
[52] U.S. Cl. ............................................................ 562/5
[58] Field of Search ................................................ 562/5

[56]               References Cited

U.S. PATENT DOCUMENTS 3,502,715   3/1970   Inoue et al. .

FOREIGN PATENT DOCUMENTS 55-43058   3/1980   Japan .
1117859    5/1989   Japan .

OTHER PUBLICATIONS

Database WPI, Section Ch, Derwent Publications, Ltd., London, GB; Class E14, AN 72–47995T (Abstract) (1972).

Database WPI, Section Ch, Derwent Publications, Ltd., London, GB; Class E14, AN 72–42271I (Abstract) (1972).

*Primary Examiner*—José G. Dees
*Assistant Examiner*—Barbara S. Frazier
*Attorney, Agent, or Firm*—Cushman Darby & Cushman

[57]              ABSTRACT

A process for producing an aromatic peroxycarboxylic acid comprising reacting an aromatic aldehyde and oxygen in the presence of at least one oxide of a transition metal selected from chromium, manganese, iron, cobalt, nickel and copper in a solvent is provided. According to this invention, aromatic peroxycarboxylic acids can safely and easily be obtained in high yield without causing decomposition of the products.

12 Claims, No Drawings

PROCESS FOR PRODUCING AROMATIC PEROXYCARBOXYLIC ACIDS

FIELD OF THE INVENTION

This invention relates to a process for producing an aromatic peroxycarboxylic acid by aerobic oxidation of an aromatic aldehyde.

BACKGROUND OF THE INVENTION

Aromatic peroxycarboxylic acids are important oxidizing agents used in various reactions such as epoxidation of olefins, oxidation of ketones to esters or lactones, phenols to p-quinones, and sulfides to sulfoxides. A heretofore known process for producing aromatic peroxycarboxylic acids involves oxidizing an aromatic aldehyde with oxygen in the presence of a catalyst. Among the proposed catalysts for this process are homogeneous catalysts, such as conjugated imines as described in Japanese Patent Publication (Kokai) Shou 55-43058 (1980), and cobalt halides as described in Japanese Patent Publication (Kokai) Hei 1-117859.

However, conducting the aforementioned process with homogeneous catalysts results in various disadvantages. The yield of aromatic peroxycarboxylic acids is low when the catalyst is based on a conjugated imine. Serious safety hazards arise when the homogeneous catalyst is a cobalt halide. The aromatic peroxycarboxylic acids are produced in high yield, but are simultaneously decomposed in the presence of the cobalt halide catalyst which increases the risk of an explosion. Consequently, these homogenous catalysts are unsatisfactory for use in producing aromatic peroxycarboxylic acids on an industrial scale.

SUMMARY AND OBJECTS OF THE INVENTION

It is an object of the present invention to provide a catalyst which provides aromatic peroxycarboxylic acids effectively by aerobic oxidation of the corresponding aldehydes and does not decompose the produced peroxycarboxylic acids. This object was achieved on the basis of the finding that by using heterogeneous transition metal oxides as a catalyst, the desired aromatic peroxycarboxylic acids are safely and easily obtained in a high yield without causing decomposition of the products.

Thus, the present invention provides a process for producing an aromatic peroxycarboxylic acid which comprises reacting an aromatic aldehyde with oxygen in the presence of at least one oxide of a transition metal selected from chromium, manganese, iron, cobalt, nickel and copper in a solvent.

DETAILED DESCRIPTION OF THE INVENTION

In the process of the present invention, aromatic aldehydes include, for instance, benzaldehyde, o-tolualdehyde, m-tolualdehyde, p-tolualdehyde, p-ethylbenzaldehyde, p-isopropylbenzaldehyde, p-tert-butylbenzaldehyde, 2,4-dimethylbenzaldehyde, 2,4,6-trimethylbenzaldehyde, p-anisaldehyde and m-chlorobenzaldehyde.

The present process is conducted in the presence of a transition metal oxide as a heterogenous catalyst. Preferred transition metal oxides are chromium(III) oxide, chromium(IV) oxide, manganese(IV) oxide, iron(III) oxide, iron(II, III) oxide, cobalt(II) oxide, cobalt(II, III) oxide, nickel(II) oxide, nickel(III) oxide, copper(I) oxide and copper(II) oxide are exemplified. Iron(III) oxide, iron(II, III) oxide, manganese(IV) oxide, copper(I) oxide and copper(II) oxide. The amount of the transition metal oxide is not particularly limited, but it is usually in a range of 0.0 to 50 mol % based on the aromatic aldehyde, and preferably is in a range of 0.1 to 10 mol %.

In the present invention, oxygen can be supplied as pure oxygen gas or molecular oxygen-containing gas such as air. The reaction can be carried out under elevated pressure or atmospheric pressure. When pure oxygen gas is used, atmospheric pressure is good enough to carry out the reaction. More particularly, when the oxygen is supplied as oxygen gas, the reaction can be carried out at atmospheric pressure, although the pressure can be from above about atmospheric to 5 atm. When the oxygen is supplied as an oxygen-containing gas, the reaction can, in general, be carried out at a pressure above about atmospheric pressure to about 100 atm, and more specifically up to 60 atm.

Exemplary solvents for use in the present process include aromatic hydrocarbons such as benzene, toluene, xylene, monochlorobenzene and dichlorobenzene, halogenated hydrocarbons such as dichloromethane, chloroform and ethylene dichloride, esters such as ethyl acetate, nitriles such as acetonitrile, ketones such as acetone and methyl ethyl ketone. The aromatic hydrocarbons are preferably used since they are easily handled from an industrial point of view.

The amount of the solvent used is determined in accordance with the reaction conditions such as the kind of the starting aromatic aldehyde and the reaction temperature and is not particularly limited. But it is usually in a range of 1 to 40 by weight and preferably is in a range of 2 to 20 times by weight based on the aromatic aldehyde used.

The reaction temperature is usually in a range of 0° to 70° C., preferably in a range of 20° to 50° C.

After the reaction, the desired aromatic peroxycarboxylic acid can easily be obtained, for example, by filtering off insoluble materials such as the transition metal oxide. When the desired compound is used as an oxidizing agent, the resulting solution can be used as it is.

According to the present invention, aromatic peroxycarboxylic acids can safely be obtained from the corresponding aromatic aldehydes in high yield without causing decomposition of the product.

The present invention is illustrated by the following examples, but the scope of the present invention is not limited to them. Analysis of the product was carried out by iodometry in each example.

EXAMPLE 1

A mixture of 0.318 g of benzaldehyde, 5 mg of iron(III) oxide and 5 ml of benzene was vigorously stirred at 25° C. under oxygen atmosphere (1 atm ) for 30 minutes.

Analysis of the reaction mixture gave the results shown below.

| | |
|---|---|
| conversion of benzaldehyde | 94% |
| selectivity of peroxybenzoic acid | 80% |
| yield of peroxybenzoic acid | 75% |

EXAMPLE 2

A mixture of 0.403 g of 2,4-dimethylbenzaldehyde, 2 mg of copper(II) oxide and 5 ml of toluene was vigorously stirred at 25° C. under oxygen atmosphere (1 atm) for 1 hour.

Analysis of the reaction mixture gave the results shown below.

| | |
|---|---|
| conversion of 2,4-dimethylbenzaldehyde | 99% |
| selectivity of 2,4-dimethylperoxybenzoic acid | 80% |
| yield of 2,4-dimethylperoxybenzoic acid | 75% |

EXAMPLE 3

A mixture of 0.408 g of p-anisaldehyde, 7 mg of iron(II, III) oxide, and 5 ml of ethyl acetate was vigorously stirred at 25 °C. under oxygen atmosphere (1 atm) for 1 hour.

Analysis of the reaction mixture gave the results shown below.

| | |
|---|---|
| conversion of p-anisaldehyde | 99% |
| selectivity of p-methoxyperoxybenzoic acid | 80% |
| yield of p-methoxyperoxybenzoic acid | 75% |

EXAMPLES 4–9

A mixture of 0.318 g of benzaldehyde, 3 mol % based on the aldehyde of a catalyst, and 3 ml of benzene was vigorously stirred at 25° C. under oxygen atmosphere (1 atm) for 1 hour.

Analysis of the reaction mixture gave the results shown in Table 1.

TABLE 1

| Example No. | Catalyst | Conversion of benzaldehyde (%) | Selectivity of peroxybenzoic acid (%) | yield of peroxybenzoic acid (%) |
|---|---|---|---|---|
| 4 | $Cr_2O_3$ | 92 | 82 | 75 |
| 5 | $MnO_2$ | 98 | 88 | 86 |
| 6 | $Fe_3O_4$ | 97 | 89 | 86 |
| 7 | $Co_3O_4$ | 91 | 84 | 76 |
| 8 | $Ni_2O_3$ | 90 | 84 | 76 |
| 9 | $Cu_2O$ | 96 | 89 | 85 |

EXAMPLE 10

The reaction mixture obtained in example 1 was allowed to stand for 24 hours at 25° C. After that, it was analyzed and the result is shown below. Decomposition of peroxybenzoic acid was not observed.

| | |
|---|---|
| conversion of benzaldehyde | 100% |
| selectivity of peroxybenzoic acid | 79% |
| yield of peroxybenzoic acid | 79% |

COMPARATIVE EXAMPLE 1 to 5

To the mixture of 100 g of a 6.2% by weight benzene solution of peroxybenzoic acid was added each catalyst shown in Table 2 and the resulting mixture was stirred for 6 hours at 25° C.

Analysis of the reaction mixture gave the results shown in Table 2.

TABLE 2

| Comp. Ex. No. | Catalyst | Amount of catalyst | Concentration of metal | Remaining ratio of peroxybenzoic acid | Remark |
|---|---|---|---|---|---|
| 1 | $COCl_2.6H_2O$ | 2.0 mg | 5 ppm | 41% | homogeneous |
| 2 | $FeCl_3$ | 1.5 | 5 | 29 | homogeneous |
| 3 | $CuCl_2$ | 1.1 | 5 | 54 | homogeneous |
| 4 | $MnCl_2.4H_2O$ | 1.8 | 5 | 22 | homogeneous |
| 5 | $Fe_2O_3$ | 0.7 | 5 | 99 | heterogeneous |

EXAMPLE 11

A solution obtained by removing insoluble materials from the reaction mixture obtained in the same manner as in example 1 was added dropwise to 98 mg of cyclohexanone at 25° C. during an hour, and at the same temperature, the mixture was stirred for 12 hours to carry out an oxidation reaction of cyclohexanone.

After the reaction, analysis of the reaction mixture gave the results shown below.

| | |
|---|---|
| conversion of cyclohexanone | 99% |
| selectivity of caprolactone | 100% |
| yield of caprolactone | 99% |

What is claimed is:

1. A process for producing an aromatic peroxycarboxylic acid comprising reacting an aromatic aldehyde with oxygen in the presence of at least one oxide of a transition metal selected from chromium, manganese, iron, cobalt, nickel and copper in a solvent, said reaction being conducted at a temperature in the range of 20° C. to 50° C.

2. The process of claim 1 in which said transition metal oxide is iron(III) oxide or iron(II, III) oxide.

3. The process of claim 1 in which said transition metal oxide is copper(I) oxide or copper(II) oxide.

4. The process of claim 1 in which said transition metal oxide is manganese(IV) oxide.

5. The process of claim 1 in which the amount of transition metal oxide used is in the range of 0.01 to 50 mol % based on the aromatic aldehyde.

6. The process of claim 1 in which the solvent is an aromatic hydrocarbon.

7. The process of claim 1 in which the amount of the solvent used is in the range of 1 to 40 times by weight based on the aromatic aldehyde used.

8. The process of claim 1 in which oxygen is supplied as pure oxygen gas or molecular oxygen-containing gas.

9. The process of claim 1 in which the reaction is carried out under elevated pressure or atmospheric pressure.

10. The process of claim 1 in which the oxygen is supplied as pure oxygen gas, and the reaction is carried out above about atmospheric pressure to 5 atm.

11. The process of claim 1 in which the oxygen is supplied as an oxygen-containing gas, and the reaction is carried out at a pressure above about atmospheric pressure to about 100 atm.

12. The process of claim 11 in which the pressure is not higher than 60 atm.

* * * * *

UNITED STATES PATENT AND TRADEMARK OFFICE
CERTIFICATE OF CORRECTION

PATENT NO. : 5,523,468
DATED : June 4, 1996
INVENTOR(S) : ODA

It is certified that error appears in the above-indentified patent and that said Letters Patent is hereby corrected as shown below:

In column 2, line 4, change "0.0 to 50" to read --0.01 to 50--.

Signed and Sealed this

Twenty-ninth Day of April, 1997

Attest:

BRUCE LEHMAN

Attesting Officer

Commissioner of Patents and Trademarks